US009877995B2

(12) United States Patent
Krauskopf (10) Patent No.: US 9,877,995 B2
(45) Date of Patent: Jan. 30, 2018

(54) FRACTIONS OF WHEY PERMEATE AND USE THEREOF FOR THE PREVENTION AND THERAPY OF TYPE 2 DIABETES AND THE METABOLIC SYNDROME (75) Inventor: Jobst Krauskopf, Barum/Krs. Uelzen (DE)

(73) Assignee: S.U.K. BETEILIGUNGS GMBH, Vienna (AT)

( * ) Notice: Subject to any disclaimer, the term of this patent is extended or adjusted under 35 U.S.C. 154(b) by 451 days.

(21) Appl. No.: 12/376,146

(22) PCT Filed: Aug. 3, 2007

(86) PCT No.: PCT/EP2007/058073
§ 371 (c)(1),
(2), (4) Date: Feb. 12, 2009

(87) PCT Pub. No.: WO2008/015275
PCT Pub. Date: Feb. 7, 2008

(65) Prior Publication Data
US 2009/0274768 A1 Nov. 5, 2009

(30) Foreign Application Priority Data
Aug. 3, 2006 (DE) .................. 10 2006 036 285

(51) Int. Cl.
A61K 38/01 (2006.01)
A23J 1/20 (2006.01)
A23L 33/18 (2016.01)

(52) U.S. Cl.
CPC ............ A61K 38/018 (2013.01); A23J 1/205 (2013.01); A23L 33/18 (2016.08)

(58) Field of Classification Search
None
See application file for complete search history.

(56) References Cited

U.S. PATENT DOCUMENTS

| 5,213,826 A | 5/1993 | Miller et al. |
| 5,639,501 A | 6/1997 | Vembu et al. |
| 5,654,019 A * | 8/1997 | Kobayashi et al. ............ 426/41 |
| 6,096,870 A * | 8/2000 | Mozaffar et al. ............ 530/366 |
| 6,399,140 B1 | 6/2002 | Allen et al. |
| 6,465,432 B1 * | 10/2002 | Han et al. ........................ 514/5.5 |
| 6,919,314 B1 * | 7/2005 | Schlothauer et al. ........ 514/15.6 |
| 7,148,034 B2 * | 12/2006 | Schlothauer et al. ........ 435/68.1 |
| 8,106,152 B2 * | 1/2012 | Reynolds et al. ............ 530/300 |
| 2002/0025361 A1 | 2/2002 | Kawachi et al. |
| 2003/0004095 A1 | 1/2003 | Reimer et al. |
| 2003/0040461 A1 * | 2/2003 | McAtee .............................. 514/1 |
| 2003/0118662 A1 | 6/2003 | Bastian et al. |
| 2003/0166866 A1 * | 9/2003 | Brody ..................... A23J 1/205 530/361 |
| 2003/0195150 A1 * | 10/2003 | Reynolds et al. ............. 514/12 |
| 2003/0202992 A1 * | 10/2003 | Fuchs ................... A23K 1/1846 424/283.1 |
| 2003/0221200 A1 * | 11/2003 | McLachlan ....................... 800/7 |
| 2004/0052860 A1 * | 3/2004 | Reid et al. .................... 424/535 |
| 2004/0162414 A1 * | 8/2004 | Santora et al. .......... 530/388.23 |
| 2004/0241664 A1 * | 12/2004 | Dekker et al. ..................... 435/6 |
| 2005/0164340 A1 * | 7/2005 | Schlothauer et al. ........ 435/68.1 |
| 2005/0175622 A1 * | 8/2005 | Edens et al. ................ 424/184.1 |
| 2006/0115538 A1 * | 6/2006 | Krauskopf et al. ........... 424/490 |
| 2006/0234942 A1 * | 10/2006 | Tauzin et al. .................... 514/16 |
| 2007/0092632 A1 * | 4/2007 | Kubow et al. ................ 426/656 |
| 2007/0116802 A1 * | 5/2007 | Germano ................ A23L 1/296 426/72 |
| 2007/0148307 A1 * | 6/2007 | Sherwood .............. A23C 21/08 426/590 |
| 2007/0243231 A1 * | 10/2007 | Krauskopf et al. ........... 424/439 |
| 2009/0123952 A1 * | 5/2009 | Slemmon ........... G01N 33/5058 435/7.94 |
| 2010/0048464 A1 * | 2/2010 | Recio Sanchez et al. ...... 514/12 |
| 2010/0056458 A1 * | 3/2010 | Cadee et al. .................... 514/14 |
| 2014/0017282 A1 | 1/2014 | Krauskopf et al. |

FOREIGN PATENT DOCUMENTS

| DE | 296 23 285 UI | 3/1998 |
| DE | 198 54 749 A1 | 5/2000 |
| DE | 100 08 880 A1 | 8/2000 |
| DE | 101 35 493 | 1/2003 |
| DE | 102 33 229 A1 | 2/2004 |
| EP | 0 591 857 A1 | 4/1994 |
| GB | 2 013 495 A | 8/1979 |
| GB | 2 013 496 A | 8/1979 |

(Continued)

OTHER PUBLICATIONS

Lipatov, N., 1973, "New physical methods for processing dairy products", Annual Bulletin-International Dairy Federation, No. 75, pp. 1-12.*
Villamiel, M., et al., 2000, "Influence of high-intensity ultrasound and heat treatment in continuous flow on fat, proteins, and native enzymes of milk", Journal of Agricultural Food Chemistry, vol. 48, No. 2, pp. 472-478.*
Garcia, M. C. et al., 1997, "Simultaneous separation of soya bean and animal whey proteins by reversed-phase high-performance liquid chromatography: Quantitative analysis in edible samples", Analytical Chemistry, vol. 69, No. 11, pp. 2217-2220.*
Garcia, M. C., et al., 1998, "Ultrarapid detection of bovine whey proteins in powdered soybean milk by perfusion reversed-phase high-performance liquid chromatography", Journal of Chromatography, A, vol. 822, No. 2, pp. 225-232.*

(Continued)

Primary Examiner — Paul Holland
(74) Attorney, Agent, or Firm — Scully, Scott, Murphy & Presser, P.C.

(57) ABSTRACT

Fractions of whey permeate, preferably made of sweet whey permeate and more preferably of hydrolyzed or partially hydrolyzed sweet whey permeate are provided, particularly for use in the production of pharmaceutical compositions, or of food, for the treatment, prophylaxis, or alleviation of glucose intolerance and insulin resistance, and thus of symptoms of the metabolic syndrome, type 2 diabetes, and complications in humans.

12 Claims, 4 Drawing Sheets (56) References Cited

FOREIGN PATENT DOCUMENTS

| | | |
|---|---|---|
| JP | 54-113409 A | 9/1979 |
| JP | 54-113442 A | 9/1979 |
| JP | 62-63553 A | 3/1987 |
| JP | 6-192079 A | 7/1994 |
| JP | 63-87944 A | 4/1998 |
| JP | 2002-37738 A | 2/2002 |
| RU | 2005 128 653 A2 | 3/2007 |
| WO | 01/37850 A2 | 5/2001 |
| WO | 03/011263 A2 | 2/2003 |
| WO | 03/105882 | 12/2003 |
| WO | 2004/009070 A1 | 1/2004 |
| WO | 2004/056207 A1 | 7/2004 |
| WO | 2005/000325 A2 | 1/2005 |
| WO | 2005/004990 A1 | 1/2005 |

OTHER PUBLICATIONS

Krusa, M., et al., 2000, "A reversed-phase high-performance liquid chromatographiC method for the determination of soya bean proteins in bovine milks", Analytical Chemistry, vol. 72, No. 8, pp. 1814-1818.*
Espeja, E., et al., 2001, "Fast detection of added soybean proteins in cow's, goat's, and ewe's milk by perfusion reversed-phase high-performance liquid chromatography", Journal of Separation Science, vol. 24, Nos. 10-11, pp. 856-864.*
Jung, Y. A, et al., 2003, "Mobile phase composition for resolving whey proteins in reversed-phase high performance liquid chromatography", Korean Journal of Chemical Engineering, vol. 20, No. 4, pp. 705-708.*
Ferreira, I., et al., 2003, "Determination of caseinomacropeptide by an RP-HPLC method and monitoring of the addition of rennet whey to powdered milk", Journal of Liquid Chromatography & Related Technologies, vol. 26, No. 1, pp. 99-107.*
Ferreira, I., et al., 2003, "Detection and quantification of bovine, ovine and caprine milk percentages in protected denomination of origin cheeses by reversed-phase high-performance liquid chromatography of betalactoglobulins", Journal of Chromatography A, vol. 1015, Nos. 1-2, pp. 111-118.*
Mota, M. V. T, et al., 2004, "Enzymatic hydrolysis of whey protein concentrates: Peptide HPLC profiles", Journal of Liquid Chromatography & Related Technologies, vol. 27, No. 16, pp. 2625-2639.*
Hearn, M. T. W., et al., 1988, "High-performance liquid chromatography of amino acids, peptides and proteins. LXXXVII. Comparison of retention and bandwidth properties of proteins eluted by gradient and isocratic anion-exchange chromatography", Journal of Chromatography, vol. 458, No. 1, pp. 27-44.*
Carles, C., et al., 1986, "Determination of gradient elution conditions for the separation of peptide mixtures by reversed-phase high-performance liquid chromatography: bovine β-casein tryptic digest", Journal of Dairy Research, vol. 53, pp. 595-600.*
Mant, C. T., et al., 1987, "Optimization of peptide separations in reverse-phase HPLC: Isocratic versus gradient elution", Chromatographia, vol. 24, pp. 565-572.*
Smithers, G. W., et al., 1996, "New opportunities for the isolation and utilization of whey proteins", Journal of Dairy Science, vol. 79, pp. 1454-1459.*
Zommara, M., et al., 1996, "Whey from cultured skim milk decreases serum cholesterol and increases antioxidant enzymes in liver and red blood cells in rats", Nutritional Research, vol. 16, pp. 293-302.*
Michaelidou, A., et al., 1998, "Isolation and identification of some major water-soluble peptides in feta cheese", Journal of Dairy Science, vol. 81, No. 12, pp. 3109-3116.*
Yamamoto, N., et al., 1999, "Purification and characterization of an antihypertensive peptide from a yogurt-like product fermented by Lactobacillus helveticus CPN4", Journal of Dairy Science, vol. 82, No. 7, pp. 1388-1393.*
Bounous, G., et al., 2000, "Whey protein concentrate and glutathione modulation in cancer treatment", Anticancer Research, vol. 20, No. 6C, pp. 4785-4792.*

Lothian, B., et al., 2000, "Treatment of obstructive airway disease with a cysteine donor protein supplement", Chest, vol. 117, pp. 914-916.*
Tong, L. M., 2000, "Antioxidant activity of whey in a salmon oil emulsion", Journal of Food Science, vol. 65, No. 8, pp. 1325-1329.*
Tong, L. M., et al., 2000, "Mechanisms of the antioxidant activity of a high molecular weight fraction of whey", Journal of Agriculture and Food Chemistry, vol. 48, pp. 1473-1478.*
Watanabe, A., et al., 2000, "Nutritional therapy of chronic hepatitis by whey protein", Journal of Medicine, vol. 31, Nos. 5-6, pp. 283-302.*
Zhang, N.T., et al., 2002, "Isolation of lactoferrin from bovine colostrum by SP-Sepharose cation-exchange chromatography", Milchwissenschaft, vol. 57, Nos. 11-12, pp. 614-617.*
Bounous, G., et al., 2003, "The antioxidant system", Anticancer Research, vol. 23, No. 2B, pp. 1411-1415.*
Kent, K. D., et al., 2003, "Effect of whey protein isolate on intracellular glutathione and oxidant-induced cell death in human prostate epithelial cells", Toxicology In Vitro, vol. 17, No. 1, pp. 27-33.*
Moatsou, G., et al., 2003, "Nitrogenous fractions during the manufacture of whey protein concentrates from feta cheese whey", Food Chemistry, vol. 81, No. 2, pp. 209-217.*
Marshall, K., 2004, "Therapeutic applications of whey protein", Alternative Medicine Review, vol. 9, No. 2, pp. 136-155.*
Moreno, Y. F., et al., 2005, "Features of whey protein concentrate supplementation in children with rapidly progressive HIV infection", Journal of Tropical Pediatrics, vol. 52, No. 1, pp. 34-38.*
Monaci, L., et al., 2009, "Mass spectrometry-based proteomics methods for analysis of food allergens", Trends in Analytical Chemistry, vol. 28, No. 5, pp. 581-591.*
Barile, D., et al., 2009, "Permeate from cheese whey ultrafiltration is a source of milk oligosaccharides", International Dairy Journal, vol. 19, No. 9, pp. 524-530.*
Dallas, D. C., et al., 2014, "Coupling mass spectrometry-based "Omic" sciences with bioguided processing to unravel milk's hidden bioactivities", Journal of Advanced Dairy Research, vol. 1, No. 2, pp. 104-126.*
Tseng, Y.-M., et al., 2006, "Whey protein concentrate promotes the production of glutathione (GSH) by GSH reductase in the PC12 cell line after acute ethanol exposure", Food and Chemical Toxicology, vol. 44, pp. 574-578.*
Reaven, G.M., "Do High Carbohydrate Diets Prevent the Development or Attenuate the Manifestations (or both) of Syndrome X? A Viewpoint Strongly Against" Current Opinion in Lipidology(1997) pp. 23-27, vol. 8(1).
Pschyrembel, Klinisches Wörterbuch (1994) 257 Edition, pp. 321.
Roche Lexikon Medizin, 4$^{th}$ Edition, published by Urban & Fischer Verlag (1999), p. 843.
Vega, G.L. et al., "Pathogenesis of Hypertriglyceridemia: Implications for Coronary Heart Disease and Theraphy" Advances Experimental Medicin (1989) pp. 311-326, vol. 243.
Soergel, K., "Acute Pancreatitis in Gastrointestinal Disease" Chapter 91, 3$^{rd}$ Edition, (Sleisenger, M.H. and Fordtran, J.S. eds) W.B. Saunders Company, Philadelphia, PA (1983) pp. 1462-1485.
Brown, M.S. et al., "Drugs Used in the Treatment of Hyperlipoproteinemias" Goodman and Gillman's The Pharmacological Basis of Therapeutics Chapter 34, 7$^{th}$ Edition , MacMillan Publishing Co., New York (1985) pp. 827-845.
Jänner, "Report of the Expert Panel on Detection, Evaluation and Treatment of High Blood Cholesterol in Adults" U.S. Department of Health and Human Services, NIH Publication No. 89/2925 (1989) pp. 74-77.
Tanne, D. et al., "Blood Lipids and First-Ever Ischemic Stroke/ Transient Ischemic Attack in the Bezafibrate Infarction Prevention (BIP) Registry" Circulation (2001) pp. 2892-2897, vol. 104.
The Diabetes Atorvastatin Lipid Intervention (DALI) Study Group, "The Effect of Aggressive Versus Standard Lipid Lowering by Atorvastatin on Diabetic Dyslipidemia" Diabetes Care (2001) pp. 1335-1341, vol. 24.
Delaney, C.A. et al., "Sensitivity of Human Pancreatic Islets to Peroxynitrite-Induced Cell Dysfunction and Death" FEBS Letters (1996) pp. 300-306, vol. 394.

(56) References Cited

OTHER PUBLICATIONS

Kim, Y.J. et al., "Purification and Characterization of Human Caseinomacropeptide Produced by a Recombinant *Saccharomyces cerevisiae*" Protein Expression and Purification (2005) pp. 441-446, vol. 41.

Kawase, et al., "Effect of Administration of Fermented Milk Containing Whey Protein Concentrate to Rats and Healthy Men on Serum Lipids and Blood Pressure" *Journal of Dairy Science* (2000) pp. 255-263, vol. 83(2).

Daali, Y. et al., "Capillary Electrophoresis and High-Performance Anion Exchange Chromatograpgy for Monitoring Caseinoglycomacropeptide Sialylation" *Journal of Pharmaceutical and Biomedical Analysis* (2001) pp. 849-856, vol. 24.

Nueu, Uwe, D., HPLC troubleshooting guide, www.waters.com/webassets/cms/library/docs/wa20769.pdf, American Laboratory and Waters Corporation (2002) accessed on Jan. 30, 2013.

Taylor, M. J. et al., "Antioxidant Acitvity of Skim Milk: Effect of Heat and Resultant Sulfhydryl Groups" J Dairy Sci, 63:1783-1795 (1980).

Taylor, M. J. et al., Antioxidant Acitvity of Skim Milk: Effect of Sinication J Dairy Sci, 63:1938-1942 (1980).

Final Office Action issued in U.S. Appl. No. 13/930,693 dated Jan. 14, 2016.

Non-Final Office Action issued in U.S. Appl. No. 13/930,693 dated Apr. 30, 2015.

Non-Final Office Action issued in U.S. Appl. No. 13/930,693 dated Oct. 6, 2016.

Fox, P.F., (Ed.)., "Developments in dairy chemistry-3: Lactose and minor constituents", Elsevier Applied Science Publishers; New York, NY (1982) pp. II-V, VII-X, and 26-27.

International Preliminary Report on Patentability issued in International Application No. PCT/EP2007/058073 dated Feb. 17, 2009.

Kosikowski and Wierzbicki, received for publication Jul. 31, 1972, Journal of Diary Science 56:1.

Macleod, A., et al. "Separation of β-lactoglobulin variants A and B from cheese whey by biospecific subunit exchange affinity chromatography" Milchwissenschaft 50 (8):440-444 (1995).

Maxilact® Product sheet, Gist-Brocades BSD B.V., Diary Ingredients Group.

Mertens und Huyghebaert, Milchwissenschaft, 1987, 42:640-642, 645.

Muthukumaran, S., et al. "Mechanisms for the ultrasonic enhancement of dairy whey ultrafiltration" Journal of Membrane Science 258:106-114 (2005).

Prenosil et al., 1987, Biotechnology and Bioengineering, 30:1026-1031.

Shah and Jelen, Milchwissenschaft, 1987, 42(12): 782-786.

Sienkiewicz, T., & Riedel, C., "Whey and whey utilization" Gelsenkirchen Buer, Verlag Th. Mann, Germany (1990) pp. 3, 4, 11, 12, 50, 261, 262, 331, 255, 368, 371 73, and 377 78.

TetraPak, Handbuch der Milch- und Molkereitechnik, 2003, Verlag Th. Mann GmbH & Co. KG, "Umwandlung von Laktose", Seiten 3, 12, 385-387 mit Deckseite (submitted with partial English translation).

* cited by examiner

FRACTIONS OF WHEY PERMEATE AND USE THEREOF FOR THE PREVENTION AND THERAPY OF TYPE 2 DIABETES AND THE METABOLIC SYNDROME

TECHNICAL FIELD

The present invention relates to the pharmaceutical and food industries. In the food industry, the area of food supplements (or functional food) is of particular importance. The prevention and treatment of insulin resistance and glucose intolerance by using fractions of whey is particularly under consideration.

Insulin resistance and glucose intolerance occur in persons, who are at risk of developing the metabolic syndrome or type 2 diabetes, or they are symptoms of the diseases already diagnosed.

According to WHO criteria, 63% of all men and 55% of all women in industrialised countries are overweight. The reason for this alarming development is the intake of excess calories from carbohydrates and fats together with further decrease in daily energy output. Even very small differences in the daily energy balance produce a large cumulative effect on body weight over years. Thus, a daily calorie intake 0.3% in excess of calorie consumption leads to a weight increase of 9.1 kg in 25 to 55-year-old Americans. Overweight people often develop the so-called metabolic syndrome (Reaven GM, Curr. Opin. Lipidol., 1997, 8 (1), p. 23-27). This refers to the simultaneous presence of overweight (obesity), high blood pressure, raised insulin level and metabolic disorder.

In scientific literature, the metabolic syndrome is also called the first early syndrome or "pre-diabetes" (Pschyrembel, *Klinisches Wörterbuch*, 257 edition (1994), p. 321).

The term "syndrome" is understood by the person skilled in the art to be a complex of symptoms, i.e. a group of illness signs that are characteristic for a specific clinical picture usually with non-uniform or unknown etiology and pathogenesis.

Further deterioration of the metabolic syndrome usually leads to type 2 diabetes developing. The dominant feature for this is an increase in blood sugar. Moreover, these diseases encourage an increased risk of secondary diseases, for example arteriosclerosis. Other health risks associated with the pathological changes from diabetes are eye problems, cardiac and vascular diseases, stroke, heart attack, kidney diseases, etc.

In past decades, the frequency of type 2 diabetes has increased dramatically. The German Federal Office of Statistics estimates that about four million people in Germany are currently affected. However, other studies are based on considerably higher figures. According to estimates from the German Diabetes Association, every tenth inhabitant of Germany will be affected by type 2 diabetes in 2006. Overweight diabetics, for the most part, also have raised blood sugar levels (cholesterol, triglycerides) and blood pressure.

In contrast to type 1 diabetes, insulin is actually produced in type 2 diabetes. However, it can no longer be properly utilised by the body. Insulin is formed in the pancreas and ensures that glucose in food gets into the cells. When glucose is supplied to the body through food and the blood sugar level in blood rises, more insulin is deposited in the blood in order to transport the glucose into the cells—the blood sugar level then falls again. If the body no longer reacts correctly to the insulin, the cells become insulin-resistant. According to Roche Lexikon Medizin, 4th edition, published by Urban & Fischer Verlag, 1999, insulin resistance is understood to mean the severe reduction in or lack of therapeutic insulin effect. There are three explanations for insulin resistance occurring. Firstly, IgG antibodies can inhibit the biological effectiveness of insulin and thereby increase the requirement to over 100 IU (international units) daily. Secondly, it can lead to increased enzymatic insulin cleavage or, thirdly, can reduce the binding of insulin to its receptors. This results in insufficient energy getting into the cells, while the blood sugar level remains high. This leads to the pancreas excreting even more insulin in order to lower the blood sugar level. The constant overproduction of insulin leads to the insulin-producing beta cells in the pancreas becoming exhausted and subsequently to a lack of insulin.

Nowadays, type 2 diabetics are often treated with oral anti-diabetic drugs. These include, for example, alpha-glucosidase inhibitors, biguanides, glitazones, glinides or sulfonyl ureas.

In addition to oral anti-diabetic drugs, it can become necessary to supply insulin to the patient. Individualised types of therapy are carried out for this purpose, which are adapted to the needs of the patient.

The treatment of the metabolic syndrome is essentially based on the patients losing weight through adjusting their diet and increased mobility. However, additional drugs are often necessary for lowering blood pressure, blood sugar and blood lipid. Estimates of the annual costs in the USA from direct expenditure and indirect costs from loss of production through the above-mentioned forms of treatment are running at a total of 98 billion dollars—and increasing.

In the special field of using whey to treat diabetes, WO 01/37850 describes a milk protein hydrolysate, particularly the use of case in oglycomacropeptide (CGMP) contained therein to treat diabetes. CGMP has a molecular weight of approximately 5000 Dalton and is not found among the peptides of the whey fractions provided according to the invention, as preliminary investigations within the scope of this application have shown. Other isolated constituents are not described.

WO 2005/004990 describes the use of whey permeate, preferably sweet whey permeate, more preferably of hydrolysed or partially hydrolysed sweet whey permeate, in the production of a pharmaceutical composition for the prevention or treatment of symptoms of metabolic syndrome, of type 2 diabetes and secondary diseases in mammals.

OBJECTS OF INVENTION

Thus, it is necessary and an object of the application to make available other means and methods of prevention and treatment of glucose intolerance and insulin resistance in order thus to prevent metabolic syndrome or type 2 diabetes and to treat these diseases. Furthermore, means are required to prevent or delay worsening of the symptoms and to alleviate or cure them.

Intensive studies carried out by the applicant have led to fractions having been identified with the desired effect from whey permeate, preferably from sweet whey permeate, more preferably from lactose-reduced and/or hydrolysed or partially hydrolysed sweet whey permeate, which possess the advantageous effects for preventing or treating metabolic syndrome, type 2 diabetes and thereby benefits secondary diseases.

The term "prevention" is hereinafter understood to mean that the occurrence of a symptom or a disease is prevented.

The term "treatment" is hereinafter understood to mean every form of treatment to improve the symptoms of disease, to delay the progression of the disease, to regress the disease or to alleviate the symptoms of the disease.

The term "pharmaceutical composition" is understood to mean every form known to the person skilled in the art. Orally administered compositions are preferred.

The term "food supplements" is understood to mean every type of food, to which whey constituents according to the invention can be added, e.g. juices, syrups, mineral water, milk products, cereal bars, herb seasoning mixtures, ready-made foods (e.g. soups, frozen products, etc.), sweets, etc.

The term "isolated fraction" is understood to mean every constituent of the whey according to the invention that has been prepared in such a way by (bio-) chemical or physical methods that it can be provided in a separate and/or isolated form. Examples of separating methods are, for example, centrifuging, filtering or chromatographic separation methods. Chromatographic separation methods are preferred.

Preferred fractions are peptide fractions. These can include one or more peptides. The peptides can be glycosylated or have other substitutions known to the person skilled in the art. Where fractions of whey permeate are mentioned hereinafter, isolated fractions are intended.

An object of the present invention is to provide fractions of whey permeate, which can be used in the prevention or treatment of the above-mentioned symptoms, particularly glucose intolerance or insulin resistance.

In an embodiment of the invention, the occurrence of metabolic syndrome or type 2 diabetes is counteracted or treated by using one or more of these whey fractions. The range of the present invention also encompasses treatment, alleviation and prevention of secondary diseases of type 2 diabetes, such as arteriosclerosis, glaucoma, xanthoma, etc.

The fractions according to the invention include preferably peptides having a mass of <5000 Dalton, preferably 100 to 4000 Dalton. Further preferred size ranges are 100 to 3500 Dalton; 200 to 3000 Dalton; 200 to 2800 Dalton; 200 to 2500 Dalton; 200, 300 or 400 to 2000 Dalton; 200 to 1700 Dalton; 200 to 1600 Dalton or 200 to 1500 Dalton. The most preferred range includes peptides of 500 to 2800 in size. The most preferred range particularly includes hydrophobic peptides from 500 to 3000 Dalton and hydrophilic peptides from 500 to 2500 Dalton.

According to a preferred embodiment of the present invention, the active whey fractions can be found among the hydrophobic or hydrophilic peptides. The hydrophobic peptides and fractions of hydrophobic peptides are preferred. Particularly preferred are fractions that include peptides having the peptide masses shown in FIGS. 1 and 2.

The fact that active fractions of the whey permeate include particularly hydrophobic peptides with the above-mentioned masses was investigated through comparative examinations of the effect of various constituents of the whey in biochemical model systems with particular relevance to what happens in diabetes.

The present invention provides fractions of whey permeate, production methods for them and the use of the fractions. In summary, it provides:

1) Method for the production of fractions of whey permeate, characterised by the steps:
 a) suspension of whey permeate,
 b) ultrasound treatment of suspended whey permeate
 c) centrifuging of suspension from step (b)
 d) chromatographic separation of supernates extracted in step (c),
 e) elution of separated fractions of the whey permeate.
2) Method according to (1), wherein the chromatographic separation is carried out by means of HPLC.
3) Method according to (1) or (2), wherein the separation is carried out using a C18 silica gel chromatography column.
4) Method according to (1) to (3), wherein the whey permeate is sweet whey permeate.
5) Method according to (4), wherein the sweet whey permeate is hydrolysed or partially hydrolysed.
6) Isolated fraction of whey permeate obtainable by the method according to (1) to (5).
7) Isolated fraction of whey permeate, according to (6), including one or more polypeptides having a mass of <5000 Dalton.
8) Isolated fraction of whey permeate according to (6) or (7), characterised in that it includes peptides that are shown in FIGS. 1 and 2.
9) Isolated fraction of whey permeate according to (6) or (7), or as shown in FIG. 1, wherein at least one of the polypeptides is hydrophobic.
10) Isolated fraction of whey permeate according to (6) or (7), or as shown in FIG. 1, wherein all polypeptides are hydrophobic.
11) Pharmaceutical composition including at least one isolated fraction of whey permeate according to (6) to (11).
12) Use of at least one isolated fraction of whey permeate according to (6) to (11) as a drug.
13) Use of at least one isolated fraction of whey permeate according to (6) to (11), in the production of a drug to prevent or treat diabetes, metabolic syndrome or secondary diseases thereof.
14) Food supplement, including at least one of the isolated fractions of whey permeate according to any one from (6) to (11).

DESCRIPTION OF FIGURES

FIGS. 1 and 2 show mass spectrograms of the hydrophobic and hydrophilic proteins/peptides of the sweet whey permeate after separation in the method according to the invention. The figures show the masses of the peptides included in the fractions on the horizontal axis, while the intensity of each peptide is indicated on the vertical axis.

DETAILED DESCRIPTION OF THE INVENTION

Isolated fractions of whey permeate are made available according to the invention, preferably including peptides of the above-mentioned masses. The whey permeate used according to the invention is preferably extracted from sweet whey.

Figure 1A:
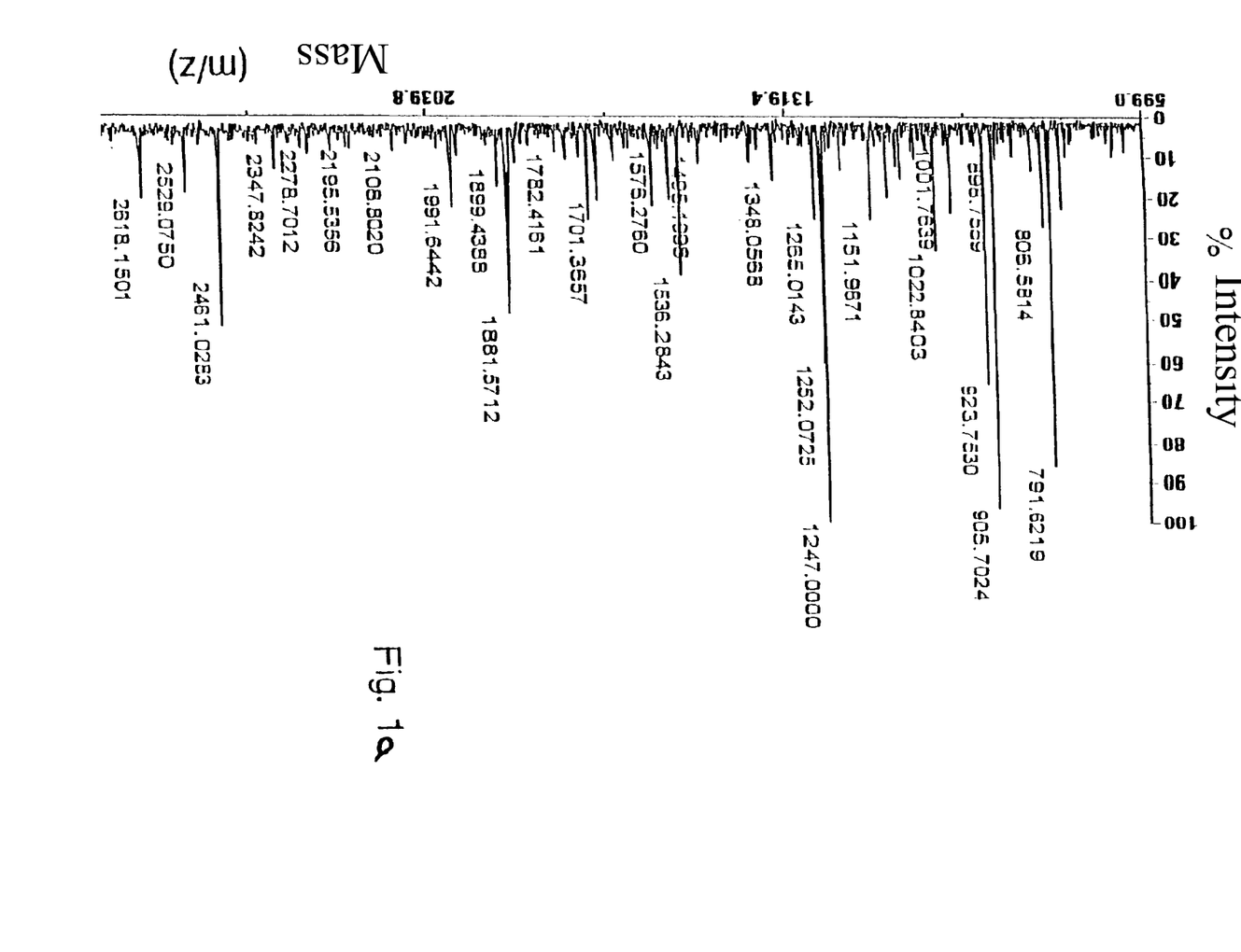
Figure 1B:
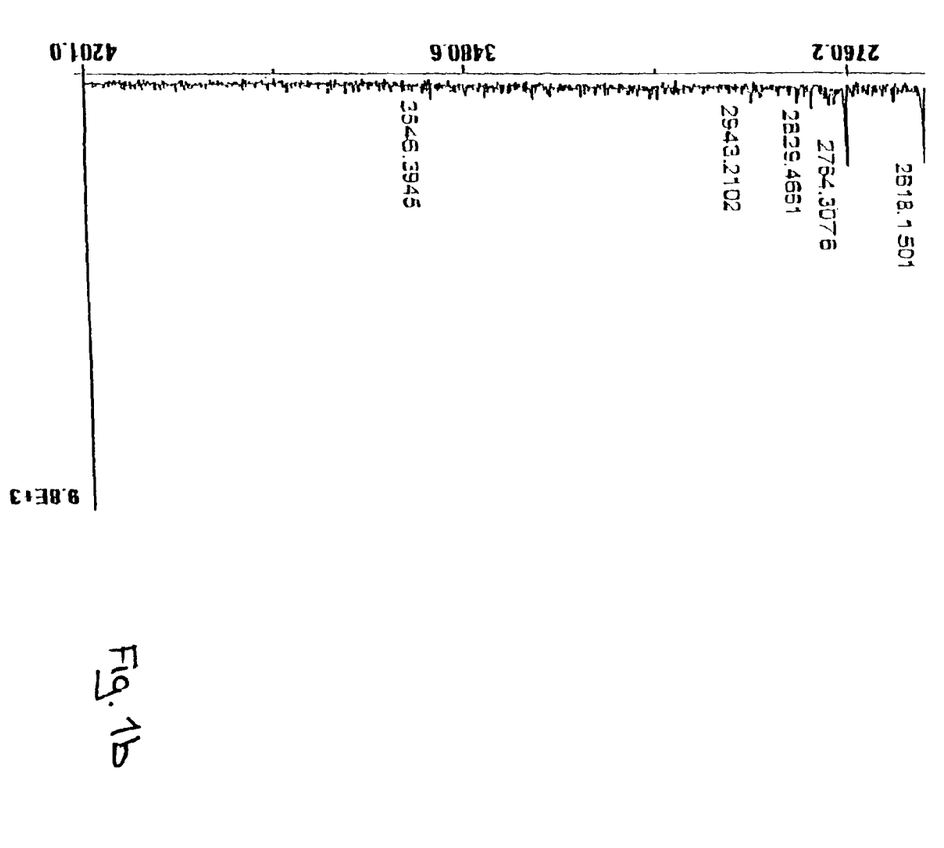
Figure 2A:
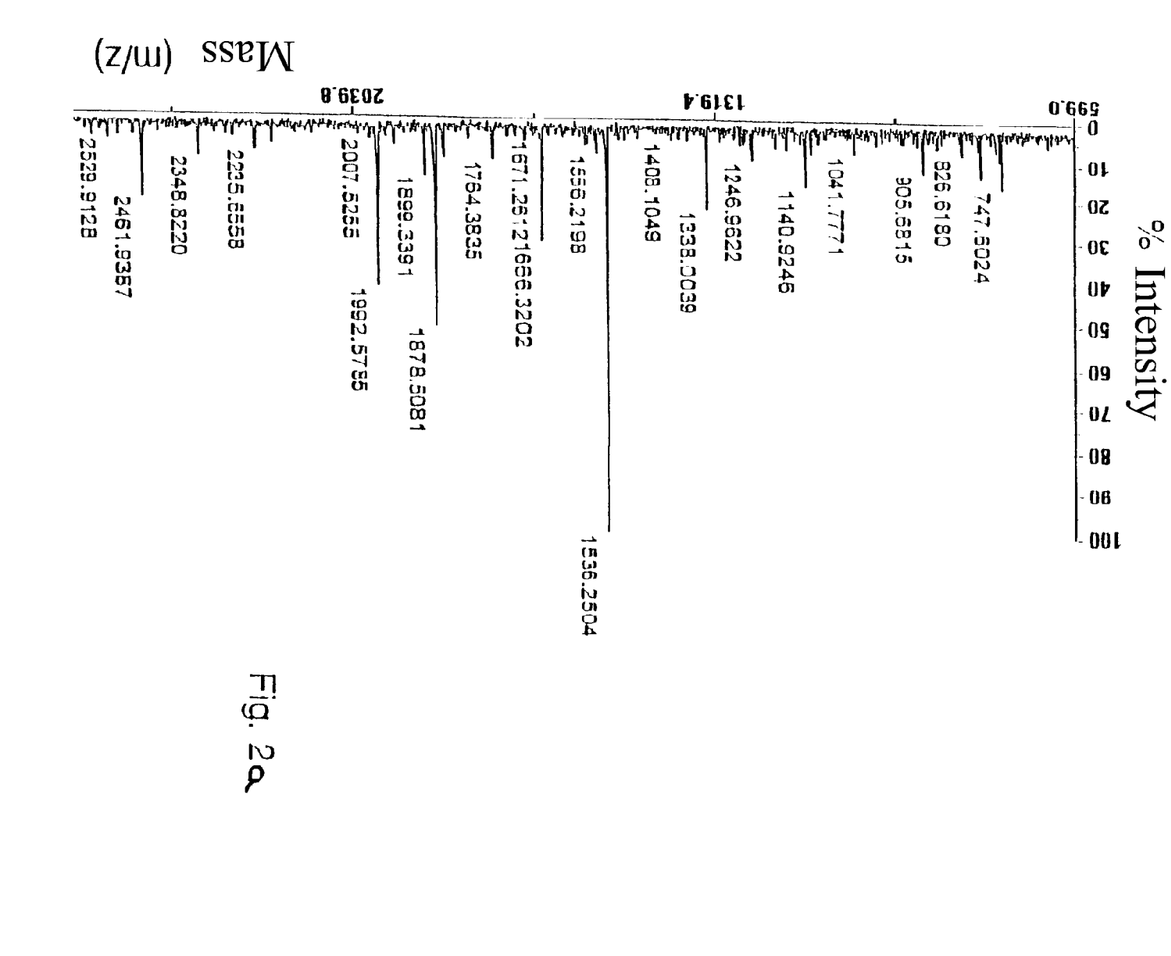
Figure 2B:
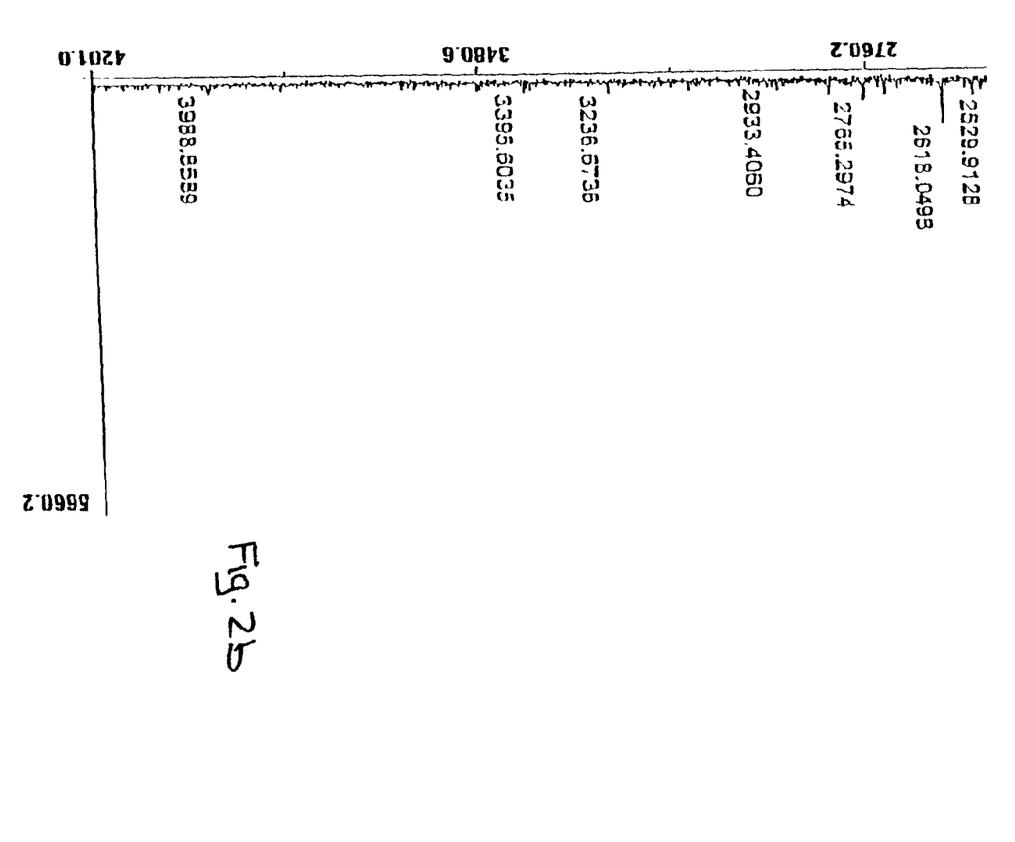

The purification of the fractions of whey permeate proved to be extremely difficult. In order to overcome the difficulties, a special HPLC purifications method was developed, which enabled the fractions according to the invention to be provided in sufficient yield and purity. This method for purifying the whey peptides is part of the invention. Firstly, the isolated fractions included in the claim could be produced by the method. Mass spectrometric results from the hydrophobic and hydrophilic whey peptide fractions obtained are shown in FIGS. 1 and 2, respectively.

The method according to the invention includes the sequence of the necessary steps given in the claims.

Necessary steps are the following steps (a) to (e):
 a) suspension of whey permeate,
 b) ultrasound treatment of suspended whey permeate
 c) centrifuging of suspension from step (b)
 d) chromatographic separation of supernates extracted in step (c), e) elution of separated fractions of the whey permeate.

Step a) relates to the suspension of powdered/non-powdered whey permeate in a medium. Examples of possible media are water, phosphate-buffered saline solution (PBS) or acidulated aqueous solutions.

Particularly preferred are acidulated aqueous solutions, particularly 0.05 to 1.0 vol. % solutions of trifluoroacetic acid, hydrochloric acid or other organic or inorganic solutions in water (e.g. bidistilled water, water for injection or Merck water (Fluka cat. no. 91699)). Most preferable are 0.05 to 0.25, particularly 0.1 vol. % solutions of trifluoroacetic acid in water.

The suspensions are produced at temperatures from 0 to 50° C., preferably at temperatures of 4 to 37° C. and particularly preferably at approx. 25° C. Suspension can be made easier by stirring. It is preferable that the reagents mixed together in a beaker are mixed on a magnetic stirrer. This step is carried out until precipitate can no longer be detected. The mixing step depends on the concentration of the whey permeate used and can last a few minutes to several hours. For a 1% suspension of whey permeate in a solvent this step lasts approx. 10 to 60 minutes, however, 30 minutes at 25° C. is usually sufficient.

Step (b) relates to the ultrasound treatment of the suspension obtained. For this purpose, the suspension obtained in a vessel is placed into a conventional ultrasound device. The vessel preferably stands or floats in an ultrasound bath and is treated for a few minutes, preferably 1 to 20 minutes. The treatment for 1 to 5 minutes, e.g. 2, 3 or 4 minutes, is generally sufficient at maximum exposure to sonic waves (e.g. 60 W). It is known to the person skilled in the art that the duration of treatment of the suspension is dependent on factors such as the output of the ultrasound test instrument, temperature, volume, etc.

In step (c), which relates to the centrifuging of the suspension obtained, insoluble or low-soluble components are separated from the soluble. Any commercially available centrifuge can be used, provided it permits a revolution speed of 5,000 to 20,000×g. Preferred are numbers of revolutions from 10,000 to 17,000×g, particularly preferred are numbers of revolutions from 12,500 to 15,000×g, e.g. 14,000×g.

The duration of this step is approx. 3 to 30 minutes, preferably 3 to 15 minutes, particularly preferably 4 to 6 minutes. At the end of the centrifugation step, the appropriately selected settings produce a whitish sediment in the test tube, above which a clear, yellowish supernate can be found.

Next, the supernates of the centrifuged suspensions are carefully drawn off using a pipette and transferred into new vessels, e.g. centrifuge tubes. Supernates from several centrifuged suspensions can be combined. The sediment is discarded.

The chromatographic separation in step (d) is carried out preferably by means of HPLC column chromatography. For this purpose, the column is first equilibrated. Liquids for equilibrating the columns are, for example, aqueous solutions of various organic or inorganic acids, preferably trifluoroacetic acid. However, solvents other than water are conceivable for the acids and preferably the solvent is an aqueous acetonitrile solution. The concentration of each solution is adapted to suit.

Thus, for example, a concentration of 0.01 to 0.25 vol. %, particularly 0.05 to 0.2, particularly preferable 0.1 vol. % trifluoroacetic acid in a 10 to 30, preferably 15 to 25, more preferably a 20 vol. % aqueous acetonitrile solution is desired. The most preferred is a solution of 0.1 vol. % trifluoroacetic acid in a 20 vol. % aqueous acetonitrile solution (later called solution B). The water corresponds to that in step (a).

The equilibrating liquid is aspirated by a syringe and put on a chromatography column. The solution (15 ml is sufficient, but slight deviations from this amount depending on the liquid used are possible) is pushed through the column. During the intensive investigations to provide the fractions according to the invention, it became evident that a Sep-Pak column (Waters) with a C18 packing was very important. Equivalent columns from other manufacturers can be used, but the packing must correspond essentially to a C18 column, as otherwise, surprisingly, no or only a small yield of utilisable peptides could be extracted. The flow-through, a clear solution that is flushed through the column is discarded.

Next comes another equilibrating step, which essentially corresponds to the previous one and is carried out using a liquid that essentially corresponds to the liquid for the suspension of the whey permeate in step (a). It is precisely this solution that is preferred.

Next, the supernates extracted as above from step (c) are aspirated by a fresh syringe and slowly and continuously pushed through the column. In this arrangement, the column discolours in the upper part more or less strongly—depending on the used amount of the whey permeate used initially. In this way, the constituents of the supernate extracted in step (c) are chromatographically separated. The flow-through is discarded again.

The next step is for the separated fractions to be eluted (step (e)). First the hydrophilic peptide fraction is extracted. For this purpose, a syringe is filled with an essentially similar solution to that in the second column equilibrating step. The particularly preferred eluent is the above-mentioned solution B (0.1% trifluoroacetic acid in 20% aqueous acetonitrile solution). It is sufficient if 1 ml solution is used for eluting, although larger amounts can also be used, e.g. 1.5, 2.0 or 2.5 ml, etc.

The eluted fraction is collected in a vessel, e.g. in an Eppendorf tube. For a volume of 1 ml elution solution, it is characteristic that initially approx. 0.5 ml of a clear eluate is extracted and subsequently 0.5 of a yellowish eluate.

Next the hydrophobic constituents, which have been chromatographically separated in the column, are eluted—similar to extracting the eluate for the hydrophilic fraction. For this purpose, a syringe is filled with a solution of an organic or inorganic acid (e.g. trifluoroacetic acid, 0.1%) in a higher-percentage acetonitrile solution (e.g. at least 50, better 60, even better 70, preferably a 80% acetonitrile solution in water (hereinafter solution C) and the contents slowly and continuously pushed through the column. The yellowish eluate is again collected.

The equilibrating and elution steps are repeated as often as desired, whereby the same or another column can be used. The eluates extracted are combined and form either hydrophilic or hydrophobic pools. The vessels with the eluted fractions are placed open into a lyophilising device and rotated to a dry state at 4° C. Devices known to the person skilled in the art can be used for lyophilising.

The dried peptide extract can be stored at −20° C. or it can be dissolved again. For this purpose, aqueous buffers or other solvents known to the person skilled in the art can be used. Preferred are buffers with a composition of guanidinium hydrochloride (e.g. 1.0-1.5 M, preferably 1.1 M), tris (50-70 mM, preferably 55 mM), NaCl (10 to 20 mM, preferably 15 mM), KCl (0.70 to 0.95 mM, preferably 0.88 mM, $MgCl_2$ (350 to 450 mM, preferably 400 mM), EDTA (0.5 to 1.5 mM, preferably 1 mM), GSH (reduced glutathione; 2.0 to 2.8 mM, preferably 2.4 mM), $CaCl_2$ (350 to 450 mM, preferably 400 mM), polyethylene glycol (5-15, preferably 10 mM, pH $8.2_{E\text{-}buffer}$ −70 mV)), the following composition is the most preferred: 1.1 M guanidinium hydrochloride, 55 mM tris, 15 mM NaCl, 0.88 mM KCl, 400 mM $MgCl_2$, 1 mM EDTA, 2.4 mM GSH (reduced glutathione), 400 mM $CaCl_2$, 10 mM polyethylene glycol (pH $8.2_{E\text{-}buffer}$ −70 mV)). An additional preferred buffer includes 10 to 100 mM, preferably 50 mM tris/HCl (pH 7.0) in bidistilled water.

The re-suspended peptide extracts can be used for the functional experiments.

The alternatives set forth in the method steps shown above for the buffer compositions, the duration of the individual steps and the physical conditions pertaining to each (temperature, number of revolutions, volume of substances used, etc.) can be combined together in various ways. At the end of each step, suspensions or liquids are extracted, whose appearance provides the person skilled in the art with a check on whether the selected parameters have been correctly selected for an optimum yield. Whenever the solutions obtained do not have the described appearance, e.g. not the desired colour (e.g. after elution) or they are not clear (e.g. after the whey permeate is re-suspended), it can be assumed that sub-optimum conditions have been selected, which can certainly be suitable for leading to the desired peptide fractions, but which are not quantitatively or qualitatively in accordance with the method according to the invention.

It is also possible to repeat individual or several steps, if this is desired.

A mass spectrometric analysis is carried out according to a method known to the person skilled in the art.

The peptide fractions shown in FIGS. 1 and 2, which have been produced using the method according to the invention, also form part of the present invention. Their use in the compositions according to the invention also forms part of the invention.

The peptide fractions according to the invention particularly preferred include essentially at least one or more peptides with the following masses:

Masses of the peptides in the hydrophobic fraction in Dalton:
791, 905, 923, 1023, 1118, 1247, 1391, 1489, 1590, 1702, 1782, 1882, 1980, 2043, 2108, 2206, 2461, 2622, 2785

Masses of the peptides in the hydrophilic fraction in Dalton: 654, 747, 875, 954, 1041, 1179, 1253, 1338, 1366, 1434, 1500, 1536, 1666, 1698, 1827, 1861, 1986, 2023, 2185, 2315.

Slight fluctuations in the peptide yields and in the composition depend on the type of sweet whey natural product used, but also form part of the fractions according to the invention.

According to the invention, additional pharmaceutical compositions or drugs as well as food supplements are provided, which include one or more fractions of whey permeate according to the invention, particularly sweet whey permeate.

Pharmaceutical compositions according to the invention are used in the prophylaxis, treatment or prevention of glucose intolerance and insulin resistance. Moreover, in this way the symptoms of metabolic syndrome or of type 2 diabetes and the secondary diseases associated with them can be treated, alleviated or prevented in mammals, preferably humans.

Examples of secondary diseases, which accompany the metabolic syndrome or diabetes or whose occurrence is promoted by these diseases, are vascular diseases, coronary failure, arterial occlusive diseases, myocardial infarction, xanthomas, abdominal disorders, hepatosplenomegaly, pancreatitis, retinal lipaemia and/or stroke.

Whey accumulates in cheese production from milk. According to the invention, cow's milk, goat's milk, sheep's milk, buffalo's milk and camel's milk can be used to extract whey, after the casein present in the milk has been precipitated. Depending on the way it is extracted, there is a differentiation between sweet whey, which comes from milk serum following enzymatic precipitation of casein by lab fermentation, and acid whey, which is extracted after separating the casein by acid precipitation. The boundary between the pH values of sweet and acid whey is not very clearly demarcated and lies generally above or below a range of 5.6 to 5.9.

The whey used to extract the fractions according to the invention contains all water-soluble constituents of milk, provided these are not precipitated by lab or acid. In a particular embodiment sweet whey is used, which contains approx. 4.9% lactose, 0.8% protein, 0.5% mineral nutrients, 0.2% milk fat and 0.2% lactic acid.

The milk protein can be separated from the whey using ultrafiltration (membrane method, average pore size: 25 to 100 kilo Daltons, kD). This "de-proteinised" whey consists of about 95% water and can be pulverised by spray drying. This powder is called whey permeate here. In the present invention, the use of whey permeate extracted from sweet whey is preferred. The constituents contained on average therein are 84.9% lactose, 4.5% protein, 0.1% fat and 7.5% mineral nutrients. The remainder consists of non-separated water. These quantities are average values, which can vary by 5-10% (relatively) depending on the method of production.

Whey permeate can be used as such or after (partial) hydrolysis of the lactose. Preferred dosage forms for the whey are syrups or powders, but other dosage forms are also possible. According to the invention, the sweet whey is used both hydrolysed and partially-hydrolysed before the production of the fractions according to the invention.

In a further embodiment according to the invention, a micro-encapsulation of the pharmaceutical composition, which includes fractions of whey permeate, has proved particularly advantageous. The micro-encapsulation can be done as described for instance in the unexamined patent applications DE 198 54 749 A1 and DE 100 08 880 A1 and the utility model DE 296 23 285 U1. In this arrangement, the compound is securely enclosed, for example, in an envelope made of a polysaccharide, such as, for example, alginate. In order that the possibly indigestible envelope material does not prevent the release of the compound, thus making it impossible for the organism to have a nutritional physiological benefit, a digestible component, such as, for example, starch, can be added to the covering. By skilful selection and/or combination of the soluble and insoluble covering components, the administration of the micro-encapsulated pharmaceutical composition can be directed in a targeted manner to different areas of the digestive tract, A graduated release in the intestine, e.g. a release of 50 to 80 wt. %, preferably 60 to 70 wt. %, particularly 62.5 wt. % in the small intestine, and a release of 20 to 50 wt. %, preferably 30 to 40 wt. %, particularly about 35 wt. % in the large intestine, is a possible type of targeted release. A further advantageous effect can be obtained from extended durability by protecting the encapsulated compound, e.g. from environmental influences.

Moreover, the use of sweet whey permeate, from which the lactose has been partially or completely removed, is preferred according to the invention in the methods for producing the products and compositions. This sweet whey permeate is called lactose-reduced sweet whey permeate here. Sweet whey permeate normally consists of approx. 85% lactose, which can however be extracted from it for further use. What remains is therefore lactose-reduced sweet whey permeate, which includes between 0.1 and 80%, preferably between 1 to 50%, more preferably between 5 and 25% of lactose. Particularly preferable is lactose-reduced sweet whey permeate, which still includes 10 to 20% of lactose.

The present invention additionally makes available preparations, which have the following effects on symptoms of metabolic syndrome or type 2 diabetes:

preventing glucose intolerance from occurring,
preventing insulin resistance,
lowering the serum insulin level,
lowering the islet volume of the pancreas,
reducing the volume of beta cells in the pancreas,
preventing neogenesis of beta cells in the pancreatic tract epithelium,
preventing hyperinsulinism from developing,
preventing an inflammation of the pancreas pancreatitis) or inflammation of an islet and/or selected beta cell (insulitis)

A further goal is the use of compositions and products from whey permeate according to the invention to prevent and/or treat type 2 diabetes, especially to slow down the progression of the disease, preferably to improve its symptoms.

In WO2005/004990, it was surprisingly discovered that there is a morphological correlation for hyperinsulinism. This means that it leads to an increase in β-cell volume, to the appearance of small β-cell clusters in the exocrine pancreas, to the evidence of β-cells in the pancreatic duct epithelium (indication of neogenesis) and an increase in the rate of mitosis of β-cells. This morphological correlation means increased demands on this organ, which are partially compensated for by cell proliferation in order to utilise the excess metabolisable energy, for example. In addition, it was proven that administering whey permeate leads to a prevention in the rise of β-cell volume, and that these substances lead to a reduction in the islet volume in the pancreas. The administration of the pharmaceutical compositions and food supplements of this invention for these purposes is therefore preferably included within the scope of protection.

The use of whey permeate fractions leads preferably according to the invention to a lowering in blood lipid values, particularly to a lowering of the triglyceride concentration.

Furthermore, pharmaceutical compositions are included in the scope of the patent, which include one or more whey permeate fractions and one or more additional active substance(s) to lower serum insulin levels. These active substances are alpha-glucosidase inhibitors, biguanides, glitazones, sulfonyl ureas, glinides or insulin.

The use of whey permeate fractions and the use of pharmaceutical compositions that contain further active substances in addition to the whey permeate is also made available within the framework of this invention, as long as the additional active substances do not exercise a negative influence on the effect of the fractions of whey permeate according to the invention.

In a preferred embodiment, the fractions of whey permeate are extracted from the milk of cows, goats, sheep, buffalo, camels or other lactating animals for the prevention or treatment of glucose intolerance and insulin resistance as well as of metabolic syndrome or type 2 diabetes.

A particularly preferred embodiment is directed towards foods containing fractions of whey permeate and being present in the form of food supplements or of "functional food". Here, also, the use of fractions from (partially) hydrolysed sweet whey permeate is preferred. Food supplements are not only used for filling up or taste, but also for achieving a health-promoting effect, i.e. the consumer is supplied with substances through the food, which in general terms lead to the organism being protected from negative influences, e.g. due to lack of necessary substances (e.g. vitamins, mineral nutrients, etc.). The food supplements according to the invention are provided for the prophylaxis and treatment of diabetes and secondary diseases associated therewith. The whey fractions produced in accordance with the method according to the invention are particularly preferred in this connection.

In a further preferred embodiment, the fractions of whey permeate are used in the production of dietary and/or enriched foods and food supplements, respectively, which include suitable pharmaceutically acceptable additives. Examples of additives are colourings, taste enhancers, preservatives, binders or fillers known to the person skilled in the art.

According to the invention, the above-mentioned fractions of whey permeate can also be used to produce foods, for example dietary foods and/or food supplements, whereby these receive the property of preventing glucose intolerance and/or insulin resistance and if applicable thereby alleviating or curing the metabolic syndrome or progression of type 2 diabetes and/or the symptoms of the latter indications. Examples of such food (supplements) are milk products or fruit juices, which are enriched with compositions according to the invention, but other foods are also possible.

For the treatment and prevention of insulin resistance and/or glucose intolerance, particularly in metabolic syndrome and type 2 diabetes, by means of compositions or preparations that contain fractions of whey permeate, the dosage is varied individually if necessary depending on the disease indications, age, weight and gender of the person to be treated.

The concentration of the compositions or preparations according to the invention in dietary and/or enriched foods that contain fractions of whey permeate can vary depending on the suitable additive and/or carrier selected, whereby the organoleptic properties of the end product are particularly taken into account, Furthermore, the compositions according to the invention can be contained in a combination preparation for preventing or treating the symptoms of metabolic syndrome and type 2 diabetes. Besides the whey fractions according to the invention, a combination preparation contains particularly preferably one or more of the following substances: alpha-glucosidase inhibitors, biguanides, glitazones, glinides, sulfonyl ureas. The administering of the combination preparations can also be adapted individually to the needs of the patient. According to the invention, these combination preparations can be administered individually in 2 or more single doses or together.

In addition, the use of a composition according to the invention in the production of a drug is particularly preferred, preferably to alleviate or prevent glucose intolerance and/or insulin resistance, particularly as symptoms of metabolic syndrome and to treat and prevent the occurrence of type 2 diabetes, to prevent its progression and secondary diseases, which can arise from metabolic syndrome or diabetes.

The use of compositions according to the invention or drugs to alleviate/prevent glucose intolerance and/or insulin resistance, which are particularly symptoms of metabolic syndrome and type 2 diabetes, is particularly directed to the application on humans, but the treatment of other mammals, such as dogs, cats, horses, sheep, cows or pigs, etc. is also included in the scope of protection.

The compositions and preparations according to the invention are particularly preferably used in combating/preventing the growth of β-cells in the pancreas, the proliferation of β-cells in the pancreas, the rise in the β-cell and islet volume or pancreatitis in a mammal, particularly in humans.

Furthermore, it is particularly preferred that the use of compositions or preparations according to the invention leads to a lowering in the serum insulin level.

It is particularly preferred that the occurrence of glucose intolerance is prevented or that it is alleviated by giving compositions or preparations according to the invention.

In addition, it is preferred that the administering of the compositions or preparations according to the invention leads to a delayed rise in morning hyperglycaemia.

Furthermore, it is particularly preferred that the consumption of compositions or preparations according to the invention leads to a lowering of blood lipid values, particularly to a lowering in the concentration of triglycerides, however an influence on other blood lipids is also included in the scope of the present invention.

According to the invention, no calcium lactate is added to the pharmaceutical compositions or preparations, which include fractions of whey permeate.

A raised (>160 mg/100 ml) triglyceride content in the blood serum is termed a hypertriglyceridaemia (hyperlipaemia). This condition can play a part in the origin of arterial diseases and the development of coronary heart disease (Vega and Grundy, Adv. Ex. Med. 243, 311 (1989)). In addition, severe hypertriglyceridaemia (>1,000 mg/dl) is linked to chylomicronaemia and causes acute pancreatitis (see K. Soergel, Acute Pancreatitis in Gastronintestinal Disease 91, 3rd edition (Sleisenger, M. H. and Fordtran, J. S., eds), W.B. Saunders Company, Philadelphia, Pa., 1983, p. 1462-1485; and Brown, M. S. and Goldstein, J. L., Drugs used in the Treatment of Hyperlipoproteinemias, in Goodman and Gillman's, The Pharmacological Basis of Therapeutics 34, 7th edition (Macmillan Publishing Co., New York, 1985, p. 827-845).

Seriously raised concentrations of chylomicrons directly cause pancreatitis, which could be prevented by reducing triglycerides (U.S. Department of Health and Human Services, NIH Publication no. 89-2925, p. 74-77, Janner 1989, "Report of the Expert Panel on Detection, Evaluation and Treatment of High Blood Cholesterol in Adults"). In addition, it has been shown that the risk of a stroke in patients with coronary heart disease can be reduced by reducing the triglyceride content in the plasma (D. Tanne, et al.; Circulation 2001, 104, 2892-2897). Furthermore, the life expectancy of type 2 diabetics is shortened by a third compared to non-diabetics. This is probably directly connected to an increased level of triglycerides (Diabety Care; 2001-24, 1335-1341). It is therefore desirable to also provide a method for reducing plasma triglycerides in patients with hypertriglyceridaemia within the framework of treating symptoms of glucose intolerance and insulin resistance as well as metabolic syndrome and type 2 diabetes.

It is particularly preferable to give the compositions or preparations according to the invention by oral administration, but other dosage options are also included in the scope according to the invention, e.g. parenteral, intravenous, etc.

The concentration of fractions of whey permeate in a pharmaceutical or food supplement preparation lie between 0.01% and 99.99%, preferably between 0.1 and 99.9%, more preferably between 1 and 99%, particularly preferably between 1 and 80%, even more preferably between 10 and 80%, most preferably between 10 and 50% relative to the total weight of the food supplement and/or the pharmaceutical preparation.

The food supplement according to the invention and the pharmaceutical preparations according to the invention can be taken or administered once or several times daily, e.g. morning, noon, evening, together, before or after meals, but other dosage schedules are conceivable also.

In a particularly preferred embodiment of the present invention, the pharmaceutical compositions or food (supplements) are administered in order to prevent the occurrence of reactive oxygen species and to weaken or eliminate their negative consequences on the organism. What is understood by reactive oxygen species according to the invention is superoxide, hydrogen peroxide and hydroxyl radical.

The invention is described in more detail hereinafter through experiments, which should not restrict the range of the invention.

Experimental Section

1. Purification of Whey Peptide Fractions of Sweet Whey Permeate

Sweet whey permeate was produced by ultra-filtration over a hollow fibre tangential flow filter with a cut-off of 10 kDa. The protein content is thereby reduced, because only proteins/peptides that are smaller than 10 kDa can pass through the filter.

The peptide fractions were purified as follows:

(a) 5 g powdered sweet whey permeate was suspended in 125 ml of solution A (0.1% trifluoroacetic acid in Merck water corresponding to 500 µL trifluoroacetic acid, Fluka cat. no. 91699 in 500 ml water, VWR cat. no. 1.15333.2500). For this purpose, the reagents are mixed for approx. 30 min. at 400 r.p.m. at 25° C. in a 250 ml beaker (Schott Duran) on a magnetic stirrer until sediment is no longer visible.

(b) The beaker containing the suspension is then placed afloat in the ultrasound bath (Sonorex RK 156, Bandelin (35 kHz, 120 W) for 3 min. at maximum power (60 W). The water bath temperature is 15° C.

(c) Next, the suspension is pipetted into 12.5 ml tubes (Falcon) and centrifuged with 14,000 g for 5 min. at 25° C. (Ultra-Zentrifuge Discovery Hitachi Sorvall 90 SE, Rotor T 890). During centrifuging, a whitish sediment and a yellowish, clear supernate forms.

(d) The supernates from the centrifuged suspensions are taken off using a pipette and combined. The sediment is discarded.

(e) A fresh 20 ml syringe (Terumo Syringe 20 ml, SS+T20E5) is then filled with 15 ml of solution B (0.1% trifluoroacetic acid in 20% acetonitrile corresponding to 0.5 trifluoroacetic acid—100 ml acetonitrile, VWR cat. no. 1.00 030.2500 ad 500 ml bidistilled water). The syringe is placed on a Sep Pak column (C-18, Waters, Part no.: WAT051910) and the solution B contained therein is pushed through the Sep Pak column. Every time this step is carried out, the syringe is put onto the short end of the Sep Pak column. The flow-through, a clear solution, is discarded.

(f) A fresh 20 ml syringe with 15 ml of solution A is then drawn off, put onto the short end of the Sep Pak column and pushed through the column. The flow-through is discarded.

(g) Now 15 ml of the centrifugation supernate extracted above in (d) is drawn off using a fresh 20 ml syringe and slowly and continuously pushed through the Sep Pak column. During this process, the upper part of the column becomes yellowish. The flow-through is again discarded.

(h) Next, the hydrophilic peptide fraction is eluted in the flow-through. For this purpose, a 1 ml syringe (Omnifix F 1 ml, Roth cat. no. H999) is filled with 1 ml of solution B and pushed through the Sep Pak column. The flow-through is collected in a 2 ml reaction vessel (Eppendorf Safe-Lock, 2 ml, cat no. 0030120.094). At the start of this step, approx. 0.5 ml of a colourless liquid is eluted, then approx. 0.5 ml of a yellowish eluate escapes from the Sep Pak column.

(i) Then the hydrophobic peptide fraction is eluted in the flow-through. A fresh 1 ml syringe is filled with 1 ml of solution C (0.1% trifluoroacetic acid in 80% acetonitrile, corresponding to 0.5 ml trifluoroacetic acid+400 ml acetonitrile ad 500 ml bidistilled water) and slowly and continuously pushed through the Sep Pak column. The flow-through is collected in a 2 ml reaction vessel. A yellowish liquid is eluted.

(j) The steps (f) to (i) are repeated until the supernates extracted in step (d) are completely used up. The same Sep Pak column can be used for this purpose.

(k) Now all hydrophilic or hydrophobic peptide fractions obtained are combined.

(l) The vessels that contain the hydrophilic or hydrophobic peptide fractions are placed open into a SpeedVac (Univapo 150 H, UniEquib 5) and rotated at 4° C. until dry.

(m) The dried peptide extract can now be immediately resolubilised in native buffer 1 (1.1 M guanidinium-hydrochloride, 55 mM tris, 15 mM NaCl, 0.88 mM KCl, 400 mM $MgCl_2$, 1 mM EDTA, 2.4 mM GSH (reduced glutathione), 400 mM $CaCl_2$, 10 mM polyethylene glycol (pH $8.2_{E-buffer}$ −70 mV))) or native buffer 2 (50 mM tris/HCl (pH 7.0) in bidistilled water) and for example used for functional analyses. The peptide pellet can also be taken up in other water-soluble buffers and processed further. If necessary, the dried peptide extract can be stored at −20° C.

The qualitative yield of hydrophobic peptide fractions from 5 g of sweet whey permeate was approx. 30 mg (~0.6%). The yield of hydrophilic peptide fraction for the same original quantity of sweet whey permeate was approx. 9 mg (~0.18%).

2. Mass Spectroscopy Analysis (MS Analysis) of Peptide Fractions Extracted

The hydrophilic and hydrophobic peptide fractions extracted were qualitatively examined using mass spectrometry (Voyager—STR; reflector mode). For the MS analysis, approx. 1 μg of peptide fraction from each fraction was used. FIGS. 1 and 2 show the results of the MS analyses of the hydrophilic and hydrophobic peptide fractions, respectively.

3. In-vitro examination of the peptide fractions extracted on models with special relevance for processes in diabetes In order to ascertain the effectiveness of the samples examined, it must be ensured that identical quantities of the substance to be tested are in the reaction batches of the biochemical test systems. The reference size for this is the dry mass content. For dose-effectiveness curves, dry mass contents of 0.1-20 mg were used.

The SWP tested concerns an ultra-filtered and spray-dried whey permeate of fresh sweet whey. According to information from the manufacturer (Hafen-Mühlen-Werke GmbH, Bremen, Germany), this product is formulated as follows:

lactose: min. 83.0%
protein: 2.0. 5.0%
minerals: max. 9.0%
fat: max. 1.5%
moisture: max. 3.0%

3. Diabetes model systems used:

3.1 DHF System

With raised insulin resistance (type 2 diabetes) in the liver, gluconeogenesis and glucose transfer into the blood is not reduced despite hyperglycaemia, but increased. The glucose passes through preferably inactive, so-called frustrane metabolic cycles, without being oxidised (breakdown) or polymerised (formation of glycogen). This opens up the possibility of sugar auto-oxidation in the presence of traces of transition metals, which are accompanied by the formation of reactive oxygen species (superoxide, hydrogen peroxide, hydroxyl radical).

The auto-oxidation of monosaccharides is a very slow reaction. The speed-determining step is the formation of enediol. Monosaccharides such as glucose reduce oxygen to superoxide via their enediol tautomer. Dihydroxyfumaric acid (DHF) is an enediol and can serve as a model compound for auto-oxidising sugar.

DHF is oxidised in the model system in the presence of Cu ions. The reactive oxygen species that is found here is predominantly superoxide, but also hydrogen peroxide and the aggressive hydroxyl radical. The reactive oxygen species react with the KMB indicator molecule (alpha-keto-S-methyl-butyric acid), which breaks down into substances including ethene, which can be very sensitively detected by gas chromatography. A reduced release of ethene from KMB in the presence of test substances should be equated with a detoxification of the reactive oxygen species.

Decisive importance is attached to detoxification of the superoxide, for, firstly, superoxide serves as a precursor molecule for the formation of hydrogen peroxide and of hydroxyl radicals and, secondly, it is involved in the formation of peroxynitrite. Superoxide reacts in an extremely rapid reaction with NO while generating peroxynitrite. This compound is itself a potent oxidant and is formed by consuming NO, an endogenous vessel relaxant which inhibits the adhesion of blood monocytes to the vessel endothelium. These two functions of NO counteract atherosclerosis.

The following reaction batch was used:

| Reagent | Concentration in batch |
|---|---|
| phosphate buffer, pH 7.4 | 100 mM |
| dihydroxyfumaric acid | 0.25 mM |
| copper(II)sulfate | 0.005 mM |
| test substances | 0, 0.1-20 mg |
| KMB | 1.5 mM |
| $H_2O$ (bidistilled) ad | 2 ml |

The reaction batches are incubated in volume-calibrated, gastight, locked reaction vessels for 30 minutes at 37° C. Next, the amounts of ethene released during the reaction are quantified by gas chromatography using headspace technology.

3.2 Peroxynitrite System

Peroxynitrite is a potent cytotoxic oxidant, which is produced from the reaction of superoxide with NO. Through inflammatory processes, stimulated immune cells (macrophages) produce both NO as well as superoxide, so that peroxynitrite forms at all inflammation foci. A further common formation site of precursor molecules for peroxynitrite is the blood vessel system, where NO and superoxide, the latter by xanthinoxidase or auto-oxidising sugars, are released by the endothelium.

A fundamental mechanism of toxicity of peroxynitrite lies in the introduction of nitro groups (formation of nitrotyrosine) in proteins, which thus lose their function.

Nitrotyrosine could be detected both in islet cells as well as in the blood vessel system of diabetics. In the animal model, it was recently shown that a substance that can destroy peroxynitrite could suppress both the development of diabetes as well as cardiovascular complications (Delaney et al, FEBS Letters 394 (1996 300-306; Sensitivity of pancreatic islets to peroxynitrite-induced cell dysfunction and death). This refers to the central role of peroxynitrite in triggering the disease and in manifesting the late complications. Like other strong oxidants, peroxynitrite can split KMB, thereby releasing ethene. In the model system, synthetically produced peroxynitrite is used. Less ethene released from KMB in the presence of test substances should be equated with the detoxification of peroxynitrite.

The following reaction batch was used:

| Reagent | Concentration in batch |
| --- | --- |
| phosphate buffer, pH 7.4 | 100 mM |
| synthetic peroxynitrite | 25 μm |
| test substances | 0, 0.1-20 mg |
| KMB | 1.5 mM |
| H$_2$O (bidistilled) ad | 2 ml |

As in the first system, the reaction batches are incubated in volume-calibrated, gastight, locked reaction vessels for 30 minutes at 37° C. Next, the amounts of ethene released during the reaction are quantified by gas chromatography using headspace technology.

3.3 X/XOD System

Superoxide can also be generated enzymatically, The enzyme, xanthinoxidase XOD) reduces oxygen at the cost of xanthin (X) to a superoxide radical anion and to hydrogen peroxide. In the presence of transition metal ions (e.g. Fe$^{2+}$), which is present in traces in every buffer and in the enzyme preparation, hydrogen peroxide can be reduced to the aggressive OH radical.

In the process, Fe$^{2+}$ is converted to Fe$^{3+}$, which is however regenerated back to Fe$^{2+}$ by superoxide. This reaction sequence is called the Haber-Weiss reaction and is rated as one of the most important sources for reactive oxygen species (ROS) in vivo. Both superoxide radical anions as well as OH radicals are able, as already mentioned, to attack alpha-keto-S-methyl butyric acid (KMB) and to split this molecule by oxidation. Ethene, which can be very sensitively detected using gas chromatography, is formed as a breakdown product from this.

In vivo, the XOD is particularly active in poorly vascularised tissues and vessels, e.g. in conditions of atherosclerotic changes, which represent a chief complication[s] of Diabetes mellitus.

The following reaction batch was used:

| Reagent | Concentration in batch |
| --- | --- |
| phosphate buffer, pH 7.4 | 100 mM |
| XOD | 0.04 U |
| xanthin | 0.5 mM |
| test substances | 0, 0.1-20 mg |
| KMB | 1.5 mM |
| H$_2$O (bidistilled) ad | 2 ml |

The reaction batches are incubated in volume-calibrated, gastight, locked reaction vessels for 30 minutes at 37° C. Next, the amounts of ethene released during the reaction are quantified by gas chromatography using headspace technology.

3.4 Requirements of IC50 Values

The IC50 value can be referred to when making a direct comparison of the effectiveness of various substances in a model system. The IC50 value indicates the concentration of a substance in the batch, which leads to a half-maximum inhibition in the control reaction (without substance). The IC50 values are read off the diagram using a screen reader. For this purpose, each curve in the diagram is subjected to a sigmoidal adjustment. At the height of the 50% mark on the Y axis, a straight line is drawn parallel to the X axis. The interface of this straight line with the adjusted curve produces the concentration that corresponds to the IC50 value.

3.5 Results 3.5.1 The DHF System

By adding SWP (Hasan), formation of ethene is inhibited and thus detoxification of up to 20% of the reactive compounds formed in this system was observed. In a concentration of 1 mg and above in the batch, SWP displays excellent activity as an antioxidant.

In order to be able to breakdown the active constituents of the whey permeate in the biochemical model systems, sub-fractions were produced from the SWP and examined in the test system. The concentrations of these constituents were selected so that they correspond to their proportion of the dry substance of the SWP. Hydrophobic constituents (peptides and proteins) showed particularly good effectiveness here. Expressed in absolute figures: 75 ng hydrophobic peptides are able to inhibit the formation of reactive compounds in the DHF system by almost 60%.

4.2 The Peroxynitrite System

In the peroxynitrite system SWP did not prove to be so effective as in the DHF system, even though at high concentrations in the batch (20 mg) it detoxifies peroxynitrite by about 60%. The hydrophobic constituents proved to be the most effective of the constituents of the SWP.

4.3 The X/XOD System

In this system, SWP possesses marked anti-oxidant properties. With a concentration of 1 mg in the batch, the X/XOD system can be inhibited by over 50% by SWP. The hydrophobic constituents and the sugar fraction also had a strongly inhibiting effect.

Due to the extremely low concentration (only 0.45 μg), the effect of the hydrophobic peptide fraction does not constitute a nonspecific radical capture effect.

The results from the DHF system show that there is a lot of agreement with the X/XOD system. At 10 mg in the batch, SWP can inhibit the system to approx. 90%. The IC50 values are not quite so low, but with a maximum 2.31 mg in the batch they are still at a very low level. The hydrophobic peptide fraction also proved to be very effective.

The results from the peroxynitrite system are particularly interesting. Peroxynitrite is not a radical. It reacts preferably with proteins. Yet SWP can still have a 60% inhibiting effect at this high concentration. The hydrophobic constituents also possess a good detoxification function towards peroxynitrite.

5. Princess NINA-NFKB Reporter Gene Assay

In addition to the investigations presented above, SWP and fractions thereof were examined in an NFκB reporter gene assay (Cell Culture Service, Hamburg, Germany).

This assay is based on the following principles. Resulting from an inflammatory stimulus by TNF-α, the expression of SEAP (secreted embryonic alkaline phosphatase) is induced in the cell line A549-NFκB (CCS, Cell Culture Services, Hamburg, Germany) by activating the NFκB signalling path. As a standard for the activation, SEAP can be easily quantified in the supernate of the cells. If the test substances inhibit the activation of NFκB in their charge concentration, this can be measured by the reduced expression of SEAP.

To examine the effectiveness, different concentrations of the substances to be tested are used. The maximum concentration was 10% of the dry mass, which had been diluted in 6 steps each time 1:2 with cell culture medium from the A549 cells. The A549-NFκB are sown into 96 well plates and pre-incubated with the test substance for 20 hours. 5 mM of dexamethasone was used as the positive control, which has a strongly inhibiting effect on gene expression. The cells were then stimulated with TNF-α (10 ng/ml) in order to simulate the inflammatory reaction. The cells were cultivated for a further 24 hours at 37° C., 5% $CO_2$ and high air humidity.

The expression of the SEAP reporter gene in the culture supernate was determined as the standard for the activation of the NFκB signalling path. CSPD is converted by SEAP as substrate into a chemiluminescent product, as quantification can be carried out in a plate luminometer (Genios, Tecan). In order to exclude adulteration of the results due to toxic influences of the test substances on the cells, the latter were incubated with the vital stain, resazurin. Metabolically active cells convert the blue resazurin [into] the fluorescent-active resofurin. The conversion can be determined by means of a fluorescent reader (Genios, Tecan) at an excitation of 560 nm and an emission wavelength of 590 nm. In the evaluation, the values are standardised to the range between the unstimulated cells (0%) and the stimulated (100%) control cells.

It was established in the investigations that activation of the NFκB signalling path by TNF-α can be inhibited, depending on the concentration, through SWP and the hydrophobic peptide fraction according to the invention.

LEGEND TO FIGURES

% Intensity
Mass m/z

The invention claimed is:

1. A method for the production of antioxidant fractions comprising peptides, the method comprising:
    a) providing a whey permeate separated from milk protein;
    b) suspending said whey permeate from step a) in an acidic solution a 0.05 to 1.0 vol. % solution of trifluoroacetic acid or hydrochloric acid in water to produce a whey permeate suspension;
    c) sonicating said whey permeate suspension from step b);
    d) centrifuging said whey permeate suspension from step c) and collecting a supernatant;
    e) applying said supernatant collected in step d) to a C18 silica gel HPLC chromatography column;
    f) eluting a first, hydrophilic fraction of said supernatant from the HPLC chromatography column in step e) with a solution of 0.05 to 1.0 vol. % trifluoroacetic acid in a 10 to 30 vol. % aqueous acetonitrile solution to produce a hydrophilic fraction having antioxidant activity;
    g) eluting a subsequent, hydrophobic fraction of said supernatant from the HPLC chromatography column in step e) with a solution of 0.05 to 1.0 vol. % trifluoroacetic acid in a 50 to 80 vol. % aqueous acetonitrile solution to produce a hydrophobic fraction having antioxidant activity; and
    h) collecting said hydrophilic and hydrophobic fractions, thereby producing antioxidant fractions comprising peptides.

2. The method of claim 1, wherein said whey permeate separated from milk protein of step a) is sweet whey permeate.

3. The method of claim 2, wherein said sweet whey permeate of step a) is hydrolyzed or partially hydrolyzed.

4. The method of claim 1, further comprising, prior to step e), equilibrating said HPLC chromatography column in a first equilibration step with a first equilibrating solution of 0.01 to 0.25 vol. % trifluoroacetic acid in a 10 to 30% vol. % aqueous acetonitrile solution.

5. The method of claim 4, wherein said first equilibrating solution is a solution of 0.1 vol. % trifluoroacetic acid in a 20 vol. % aqueous acetonitrile solution.

6. The method of claim 4, further comprising, after the first equilibration step but prior to step e), a second equilibration of said HPLC chromatography column with a second equilibrating solution of 0.01 to 0.25 vol. % trifluoroacetic acid in water.

7. The method of claim 1, wherein said hydrophobic fraction is eluted in step g) with a solution of 0.1 vol. % trifluoroacetic acid in an 80 vol. % aqueous acetonitrile solution.

8. The method of claim 1, wherein said hydrophilic fraction is eluted in step f) with a solution of 0.1 vol. % trifluoroacetic acid in a 20 vol. % aqueous acetonitrile solution.

9. The method of claim 1, wherein step h) comprises separately collecting said hydrophilic fraction collected in step f) from said hydrophobic fraction collected in step g).

10. The method of claim 1, wherein said whey permeate suspension is centrifuged in step d) at 10,000 to 17,000×g for 3 to 30 minutes.

11. The method of claim 1, wherein said sonicating in step c) is conducted for 1 to 20 minutes at 60 watts.

12. The method of claim 1, further comprising lyophilizing said antioxidant fractions comprising peptides.

* * * * *